United States Patent [19]

Samuels et al.

[11] Patent Number: 5,192,279
[45] Date of Patent: Mar. 9, 1993

[54] DENTAL TISSUE CUTTING, DRILLING AND FUSING SYSTEM

[76] Inventors: Mark A. Samuels; Scott Patterson, both of 4023 Everett Ct., Duluth, Ga. 30136

[21] Appl. No.: 725,237
[22] Filed: Jun. 26, 1991

Related U.S. Application Data

[63] Continuation of Ser. No. 390,825, Aug. 8, 1989, abandoned.

[51] Int. Cl.$^5$ ............................................. A61C 5/00
[52] U.S. Cl. ...................................... 606/17; 606/16; 128/664
[58] Field of Search ................... 606/3, 16, 17, 6, 10; 128/664

[56] References Cited

U.S. PATENT DOCUMENTS

| | | | |
|---|---|---|---|
| 3,821,510 | 6/1974 | Muncheryan | 219/121 L |
| 4,185,633 | 1/1980 | Prozorov et al. | |
| 4,273,535 | 6/1981 | Yamamoto et al. | 606/17 X |
| 4,289,378 | 9/1981 | Remy et al. | 606/17 X |
| 4,503,853 | 3/1985 | Ota et al. | 606/16 |
| 4,521,194 | 6/1985 | Myers et al. | 606/10 X |
| 4,538,609 | 9/1985 | Takenaka et al. | 606/16 |
| 4,644,550 | 2/1987 | Csery et al. | |
| 4,681,396 | 7/1987 | Jones | |
| 4,702,245 | 10/1987 | Schroder et al. | |
| 4,736,745 | 4/1988 | Gluckman | |
| 4,784,135 | 11/1988 | Blum et al. | 606/3 |
| 4,836,203 | 6/1989 | Müller et al. | 128/664 X |
| 4,849,859 | 7/1989 | Nagasawa | 128/6 X |
| 4,860,172 | 8/1989 | Schlager et al. | 606/16 X |

FOREIGN PATENT DOCUMENTS

PCT/US89/-
00984 3/1989 PCT Int'l Appl.

OTHER PUBLICATIONS

A. Paghdiwala, "Application of the Erbium:YAG Laser on Hard Dental Tissues:Measurement of the Temperature Changes and Depths of Cut," 64 *ICALEO* 192-300 ('88).

R. Hibst and U. Keller, "Experimental Studies of the Application of the Er:YAG Laser on Dental Hard Substances: I. Measurement of the Ablation Rate," 9 *Lasers in Surgery and Medicine* 338-344 (1989).

U. Keller and R. Hibst, "Experimental Studies of the Application of the Er:YAG Laser on Dental Hard Substances: II. Light Microscopic and SEM Investigations," 9 *Lasers in Surgery and Medicine* 345-351 (1989).

*Primary Examiner*—Robert A. Hafer
*Assistant Examiner*—Kerry Owens
*Attorney, Agent, or Firm*—Kilpatrick & Cody

[57] ABSTRACT

A method and apparatus are described for cutting, drilling, ablating, fusing or altering dental tissues including enamel, dentine, bone, and cementium among others. Far infrared radiation of wavelengths between 2.5 and 3.2 microns are used to selectively affect dental tissue, where the radiation energy density determines whether cutting, fusing or other effects are produced. Either continuous wave or pulsed radiation can be used, a suitable IR source being an Erbium YSGG laser having an output wavelength of 2.79 microns. The exposed dental tissue is removed, fused, or otherwise affected without damage to the surrounding tissues depending on the duration of the exposure. Medical and dental applications include the removal of carious lesions and the preparation of a carious lesion for filling with an appropriate filler material, the cutting or sectioning of healthy tissue, the sealing of cracks and fissures in the hard tissues, the fusing of enamel surfaces in order to prevent decay, the removal of calculus deposits, the preparation of implant sites, the application of coatings chemically similar to the dental hard tissue by fusion induced by the radiation, sealing of root surfaces in the treatment of sensitive teeth, the sterilization root surfaces and many more natural extensions of the invention.

2 Claims, 2 Drawing Sheets

DENTAL TISSUE CUTTING, DRILLING AND FUSING SYSTEM

This is a continuation of Ser. No. 07/390,825 filed on Aug. 8, 1989 now abandoned.

TECHNICAL FIELD

This invention relates to dental procedures using infrared radiation of wavelengths greater than 2.5 microns and less than 3.2 microns, and more particularly to a method and apparatus for selectively removing or altering dental tissues including bone, enamel, dentine, cementium, calculus, soft and other tissue preferably using radiation at 2.79 microns.

BACKGROUND ART

The use of lasers in dental procedures has been pursued for some time starting with experiments conducted with the first lasers developed in the early 1960's. Unfortunately, the lasers and wavelengths available were unable to effectively act on dental hard tissues without excessive heating resulting in pulpal necrosis (tissue death). Up to the present time, these experiments were conducted with Ruby, Helium Neon, and CO2 lasers. While the pulsed and CW CO2 lasers have been found to be effective in some ways on dental tissue, they suffer from the lack of a suitable optical conduit necessary for procedures inside the mouth.

Other uses of lasers in dental procedures are described in U.S. Pat. Nos. 4,273,535, 4,521,194, 3,821,510 and 4,784,135. In U.S. Pat. No. 4,273,535 a device is described using a NdYag laser at 1.06 microns wavelength for sealing tooth surfaces to prevent tooth decay. A flexible glass fiber is used to deliver the NdYag radiation to the tooth surface under treatment. Another application of the NdYag laser is disclosed in U.S. Pat. No. 4,521,194 where the radiation is used to remove incipient carious lesions and or stains from teeth using the output from a glass fiber directly without focussing optics or handpiece. Crystals of hydroxyapatite are fused to render the tooth surface impervious with the laser at 1-100 millijoules. A handpiece for delivery of focussed laser beams and fluids is described in U.S. Pat. No. 3,821,510. In particular, a flexible light transmitting fiber, fluid conduit and adjustable focusing system is described. U.S. Pat. No. 4,784,135 describes a Far Ultraviolet system for surgical and dental use and claims to use a non-thermal ablation mechanism. In a preferred aspect of that invention, a laser having a wavelength below 200 nm is used to treat decayed teeth by a photodecomposition action.

A significant problem in the prior art is that the action of the laser beams on the dental tissues does not disclose the capability to cut enamel surfaces with a device that is practical for use in the dental clinical environment. The only known device described with the potential to cut enamel is the Far ultraviolet laser which has significant disadvantages due to the operational characteristics of the excimer lasers employed as well as limitations on transmission through optical fibers. Accordingly, it is a primary object of this invention to provide an apparatus and method for safe and efficient cutting, drilling and fusion of dental tissues without damaging adjacent living tissues.

It is another object of this invention to provide a technique for cutting, drilling, and fusion of dental tissues in a practical system that can be utilized in the dental treatment environment.

Another object of this invention is to provide a technique for sealing or fusing the surface of dental hard tissues, including root surfaces.

It is still another object of this invention to provide means for the fusion of artificially produced coatings to the surfaces of teeth.

It is a further object of this invention to provide a means of removing unwanted hard deposits of foreign material, such as calculus and plaque deposits, from the surface of dental tissues.

It is another object of this invention to provide for the cutting, and drilling of dental bone tissues in the preparation of implant sites.

It is yet another object of the present invention to provide an apparatus for dental treatment with a laser which can be aimed with an aiming reticle co-aligned to the laser beam.

Finally, it is another object of the present invention to provide a system for the selective removal of soft tissue, such as diseased gums by the action of the infrared radiation and to provide for the sterilization of gum pockets.

DISCLOSURE OF THE INVENTION

In its broadest sense, this invention relates to the use of Infrared radiation of wavelengths between 2.5 and 3.2 microns for treatment of dental tissues and more particularly to the cutting, drilling, or fusion of dental tissue surfaces. In a preferred embodiment, radiation at 2.79 microns is used. The dental tissue can be removed or treated without damage to the surrounding healthy tissue and without excessive over heating of the tooth or bone structure. The mechanism by which the various dental techniques such as cutting, drilling and fusion, are produced is dependent on the wavelength of the radiation and relates to a water absorption band found between 2.5 and 3.2 microns. The absorption at these wavelengths is thought to be responsible for the effectiveness unexpectedly in greater excess than the prior art discloses on dental tissues which contain water in various quantities and forms.

The source of the radiation can be any known source as long as the wavelength range is between 2.5 and 3.2 microns and so long as sufficient energy density is present to produce the affect on the dental tissues. While pulsed or continuous radiation can be used, pulsed radiation energy density of greater than 10 mJ/cm2 is preferred, and continuous radiation can also be used for some applications. One suitable pulsed infrared radiation source is an Erbium YSGG solid state laser providing output at 2.79 microns. The radiation at 2.79 microns is produced very efficiently by an Erbium YSGG laser and this efficiency provides an improvement in the practical usefulness of this radiation source and wavelength over other sources such as Erbium YAG at 2.94 microns. The Erbium YSGG lasers are commercially available.

These and other objects, features, and advantages will be apparent more readily from the following descriptions of the preferred embodiments.

BRIEF DESCRIPTION OF THE DRAWING

The FIG. 1 and FIG. 2 illustrate schematically one type of suitable apparatus for carrying out this invention.

BEST MODE FOR CARRYING OUT THE INVENTION

In the practice of this invention, mid infrared radiation of wavelengths between about 2.5 and about 3.2 microns and more particularly at about 2.79 microns are used to selectively remove, cut, drill or fuse dental tissues including bone formations found in and around the teeth. By "electively" is meant to effect the desired dental procedure with no unwanted tissue destruction in the adjacent or surrounding area.

The radiation is applied either as pulsed radiation or as continuous radiation although a preferred embodiment comprises pulsed radiation with a pulse length less than about 250 microsecs. The radiation applied in this manner has been observed to provide several useful changes to the structure of the dental tissues, including the removal, cutting, drilling and melting or fusion of the surface.

Figure 1:
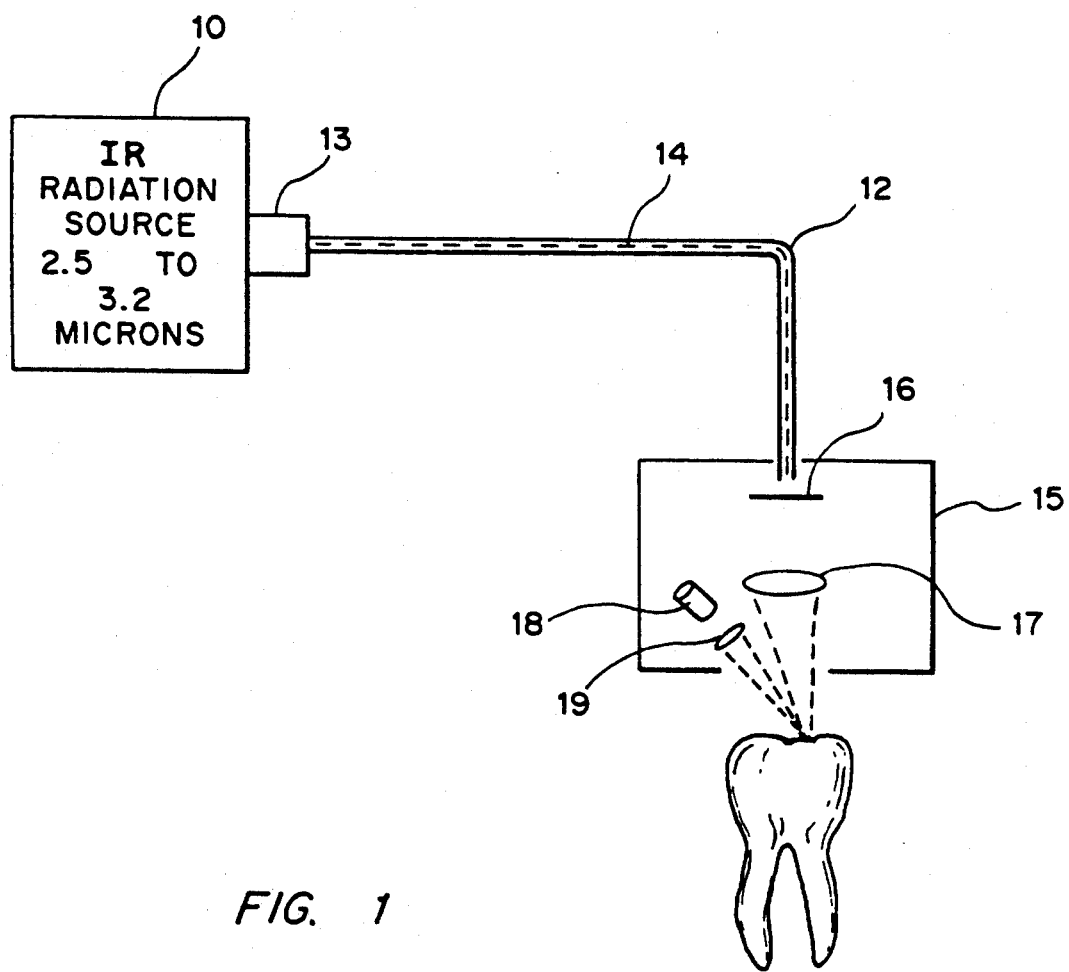
Figure 2:
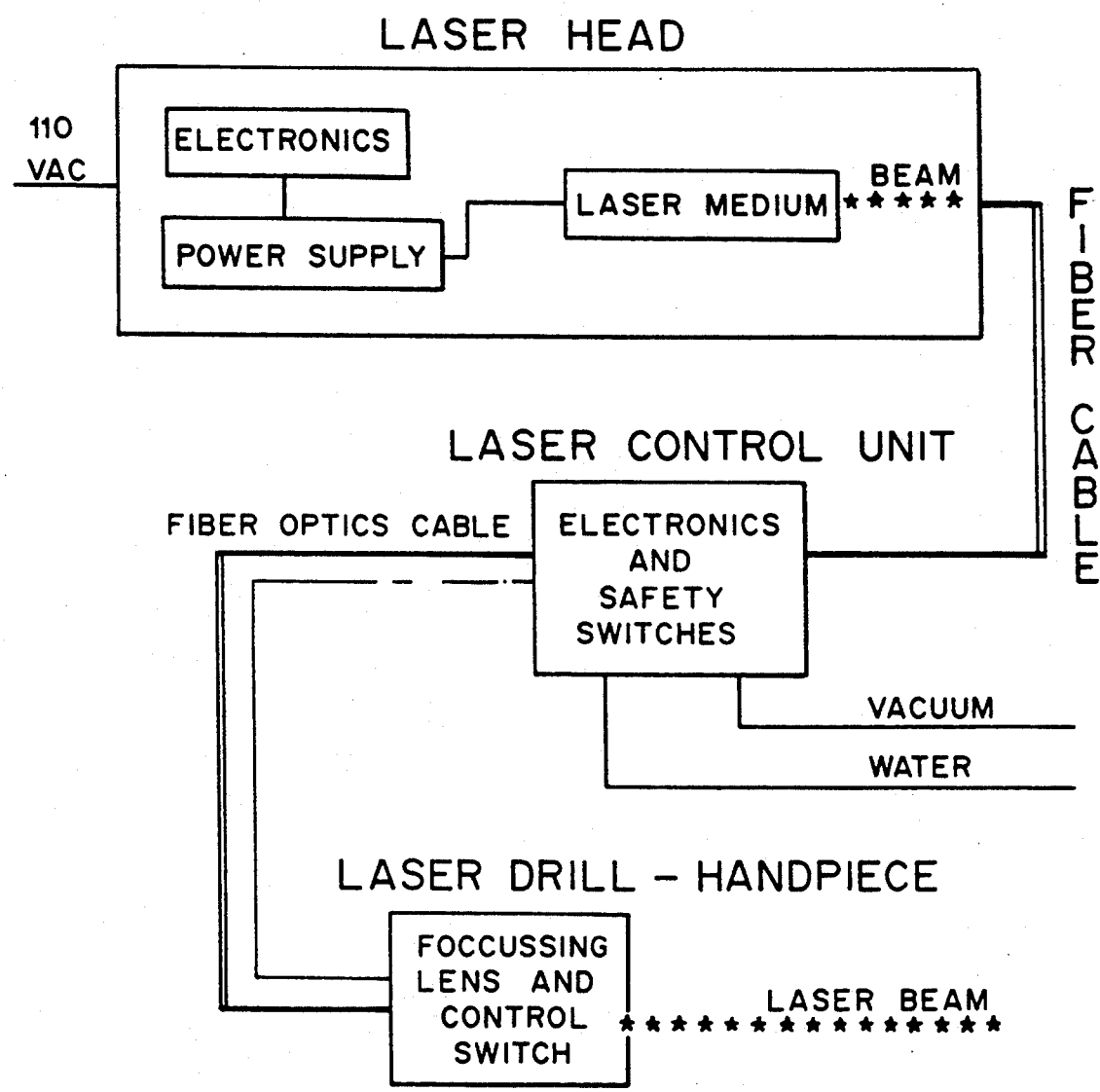

A suitable apparatus for carrying out the invention is shown in the FIG. 1. It includes a source 10 of mid infrared radiation at wavelengths between 2.5 and 3.2 microns. A suitable radiation source is an Erbium YSGG laser operating at a wavelength of 2.79 microns. The Erbium YSGG has an advantage in efficiency and is the preferred embodiment of the invention. Such lasers are commercially available and are made, for example, by Schwartz Electro-Optics, Orlando, Fla. A specific laser with desirable properties for this application is the Schwartz Electro-Optics Model ER 2790 with an output of approximately 200 mj/pulse, and a beam divergence of 3 milliradians. These lasers routinely offer repetition rates of 10 hz with a pulse width variable between 250 microseconds and 60–100 nanoseconds (Q-Switched).

A waveguide 12 is used to contain the laser beam 14 (indicated by dashed lines). A transmitting waveguide 12 is composed of a flexible optical waveguiding material such as zirconium fluoride, however, other suitable materials exist which could be used such as sapphire, or a simple articulated arm with mirrors positioned for guiding the light to the target area. The coupler 13 provides the interface between the laser and the optical waveguide 12. A casing 15, contains a shutter 16 which can be used to block the radiation beam or allow it to pass. A lens 17 is contained inside the casing for the purpose of increasing the energy density of the beam and for focussing and converging the radiation laser beam onto a selected surface of the dental tissue.

An aiming reticle 18 and projection optic 19 is provided for indicating the direction and focus of the invisible infrared beam.

For the exact design of a flexible casing, reference is made to the aforementioned U.S. Pat. No. 3,821,510 which shows a flexible laser-beam transmitting conduit that is capable of being held by hand.

The following will detail some examples of the dental applications of the technique of the present invention.

In a first application, dental enamel is removed by the action of a tightly focussed beam at 2.79 microns in the preferred embodiment for the purpose of exposing and repairing a carious lesion. As is known, teeth have an outside protective layer of Hydroxyapatite with contains calcium, phosphate and significant quantities of chemically bound water. The action of the infrared radiation herein disrupts the crystal structure of the hydroxyapatite and reduces the tooth enamel to a powder and to volatile products which escape. The infrared laser energy is effective on the tooth enamel and other dental tissues including bone due to the water absorption band found at the effective wavelengths. The laser is operated with a pulse width of less than 250 microseconds in order to reduce the perception of pain associated with the treatment. Once exposed, the carious lesion is selectively removed using a less tightly focussed beam so as not to disturb the underlying sound enamel. Once opened and cleaned, the affected area can be repaired with conventional dental techniques.

An additional aspect of this invention is in the sealing of dental tissue surface, including root surfaces for the treatment of hypersensitivity and the sealing of enamel surfaces for repair of cracks and fissures as well as the prevention of tooth decay. Examples using both Erbium Yag and Erbium YSGG, indicate that it is possible to melt the surface of root or tooth enamel to a depth of only a few microns using the pulsed laser energy at a low energy density. The melted area recrystallizes as it cools resulting in a fused, hardened surface that is resistant to seepage and fluid transport through the fused region. In the case of the root surfaces, the fused region reduces the sensitivity experienced by persons with damaged root surfaces (cut or open tubals). In the case of the enamel surfaces, fusion and recrystallization has been shown to be effective at reducing the incidence of cavities.

Another application of the invention is in providing a means of application of artificially produced coatings to the surfaces of teeth by the fusion of the coating to the tooth surface. In this application, the infrared radiation source is directed at a coating made primarily from powdered hydroxyapatite (mineral found in tooth enamel) or other suitable material. The coating, having been previously applied to a tooth surface, is fused in place by the melting of the powdered coating along with the surface of the tooth enamel in such a way as to produce a weld of high strength and durability. The coating then becomes an integral part of the tooth surface in contrast to the prior art teachings which suffers the shortened lifespan and decreased durability of cosmetic dental procedures.

Another application of this invention is to provide a means of removing unwanted foreign materials and hard deposits, such as calculus and plaque deposits, from the surface of tooth enamel or root surfaces. The calculus deposits are composed of hydrated calcium and phosphates which absorb energy at the wavelengths described. These deposits are not structurally the same as healthy tooth material and are removed by the action of the laser beam.

In another application of this invention, implant sites can be prepared by the precise cutting of bone associated with dental support structures, necessary for good integration of prosthetic implants. The advantage of the present invention lies in its ability to provide sharp, well defined cuts which are precisely matched to the implant dimensions. The resulting fit enables rapid integration of the implant into the bone structure.

Another application of this invention is in the removal of diseased gum tissue wherein the infrared radiation is able to cut living or dead gum tissue without excessive bleeding and in an auto-sterilizing manner.

In the practice of this invention, any type of dental application can be undertaken using absorption of radiation between the wavelengths of 2.5 and 3.2 microns and more particularly to 2.79 microns. While the invention has been particularly described with respect to certain embodiments and applications, it will be readily apparent to those of skill in the art that other applications can be made without departing from the spirit and scope of this invention. Further, the exact apparatus for transmitting the infrared radiation to the organic matter can be varied by those skilled in the art, without departing from the spirit and scope of this invention.

What is claimed is:

1. A method for cutting the enamel of a human tooth and removing carious lesions without damaging the nerve and pulp of the tooth, comprising the steps of:
   a. providing an Erbium YSGG laser oscillator;
   b. projecting a pulsed output from the Erbium YSGG laser oscillator, which pulsed output has (1) a wavelength of approximately 2.79 microns, (2) a pulse width of less than approximately 250 microseconds, (3) an energy of approximately 200 millijoules and (4) a repetition rate of approximately 10 pulses per second;
   c. transmitting the pulsed output projected from the laser oscillator to a condensing lens;
   c. transmitting the condensed pulsed output via an optical waveguide; and
   d. variably convergently irradiating the transmitting pulsed output via a focusing lens upon the enamel to be cut, thereby disrupting the crystal structure of the enamel and exposing the carious lesion for removal.

2. An apparatus for the treatment of dental tissue, comprising:
   a. an Erbium YSGG laser oscillator for providing a pulsed output comprising:
      i. a wavelength of 2.79 microns;
      ii. a pulse width of less than approximately 250 microseconds;
      iii. an energy of approximately 200 millijoules;
      iv. a repetition rate of approximately 10 pulses per second; and
      v. a beam divergence of no more than approximately 3 milliradians;
   b. a condensing lens for transmitting the pulsed output projected from the laser oscillator;
   c. an optical waveguide, composed of a material selected from the group consisting of zirconium fluoride and sapphire, for transmitting the condensed pulsed output; and
   d. means for cutting the enamel of a human tooth and removing carious lesions without damaging the nerve and pulp of the tooth, comprising:
      i. a casing connected to the waveguide;
      ii. a shutter contained within the casing, for selectively permitting the condensed pulsed output to pass into the casing; and
      iii. a focusing lens contained within the casing, for variably convergently irradiating the transmitted pulsed output upon the enamel to be cut, thereby disrupting the crystal structure of the enamel and exposing the carious lesion for removal.

* * * * *

UNITED STATES PATENT AND TRADEMARK OFFICE
CERTIFICATE OF CORRECTION

PATENT NO. : 5,192,279

DATED : March 9, 1993

INVENTOR(S) : Mark A. Samuels

It is certified that error appears in the above-identified patent and that said Letters Patent is hereby corrected as shown below:

Column 3, line 9, delete the word "electively" and substitute --selectively-- therefor Column 5, line 27, delete the word "transmitting" and substitute --transmitted-- therefor Signed and Sealed this Thirtieth Day of November, 1993

Attest:

*Attesting Officer*

BRUCE LEHMAN

*Commissioner of Patents and Trademarks*